US007183053B2

(12) United States Patent
Gocke et al.

(10) Patent No.: US 7,183,053 B2
(45) Date of Patent: *Feb. 27, 2007

(54) METHODS FOR DETECTING PAPILLOMAVIRUS DNA IN BLOOD PLASMA AND SERUM

(75) Inventors: Christopher D. Gocke, Ellicott City, MD (US); Neil Christensen, Harrisburg, PA (US)

(73) Assignee: The Penn State Research Foundation, University Park, PA (US)

( * ) Notice: Subject to any disclaimer, the term of this patent is extended or adjusted under 35 U.S.C. 154(b) by 567 days.

This patent is subject to a terminal disclaimer.

(21) Appl. No.: 10/328,816

(22) Filed: Dec. 24, 2002

(65) Prior Publication Data

US 2003/0175770 A1 Sep. 18, 2003

Related U.S. Application Data

(60) Division of application No. 09/653,644, filed on Aug. 31, 2000, now Pat. No. 6,511,805, which is a continuation-in-part of application No. 09/456,222, filed on Dec. 7, 1999, now Pat. No. 6,630,301, which is a continuation-in-part of application No. 09/049,234, filed on Mar. 27, 1998, now abandoned, which is a continuation-in-part of application No. 08/818,058, filed on Mar. 14, 1997, now Pat. No. 6,156,504.

(60) Provisional application No. 60/028,180, filed on Oct. 15, 1996, provisional application No. 60/026,252, filed on Sep. 17, 1996, provisional application No. 60/013,497, filed on Mar. 15, 1996.

(51) Int. Cl.
C12Q 1/68 (2006.01)
C12P 19/34 (2006.01)

(52) U.S. Cl. .......................................... 435/6; 435/91.2
(58) Field of Classification Search .................... 435/5, 435/91.2
See application file for complete search history.

(56) References Cited

U.S. PATENT DOCUMENTS

| 4,965,188 | A | 10/1990 | Mullis |
| 5,182,377 | A | 1/1993 | Manos |
| 5,283,171 | A | 2/1994 | Manos |
| 5,496,699 | A | 3/1996 | Sorenson |
| 5,512,439 | A | 4/1996 | Hornes |
| 5,512,441 | A | 4/1996 | Ronai |
| 5,527,676 | A | 6/1996 | Vogelstein |
| 5,527,898 | A | 6/1996 | Bauer |
| 5,639,871 | A | 6/1997 | Bauer |
| 5,705,627 | A | 1/1998 | Manos |
| 5,814,448 | A | 9/1998 | Silverstein |
| RE36,713 | E | 5/2000 | Vogelstein |
| 6,090,566 | A | 7/2000 | Vogelstein |
| 6,329,179 | B1* | 12/2001 | Kopreski ................... 435/91.2 |
| 6,521,409 | B1* | 2/2003 | Gocke et al. .................. 435/6 |
| 6,759,217 | B2* | 7/2004 | Kopreski ................... 435/91.2 |
| 6,916,634 | B2* | 7/2005 | Kopreski ................... 435/91.2 |
| 6,939,671 | B2* | 9/2005 | Kopreski ........................ 435/6 |
| 6,939,675 | B2* | 9/2005 | Gocke et al. .................. 435/6 |

FOREIGN PATENT DOCUMENTS

| WO | WO 89 00206 | 11/1989 |
| WO | WO 96 15139 | 5/1996 |
| WO | WO 95 16792 | 6/1996 |
| WO | WO 97 34015 | 9/1997 |
| WO | 97/35589 | * 10/1997 |

OTHER PUBLICATIONS

Aggarwal, et al., (Mar. 1975) "Cell-Surface-Associated Nucleic Acid in Tumorigenic Cells Made Visible with Platinum-Pyrimidine Complexes by Electron Microscopy." *Proc. Nat. Acad. Sci.*, vol. 72, No. 3, pp. 928-932.

Aoki et al., (Sep. 1995) "Liposome-mediated *in vivo* Gene Transfer of Antisense K-ras Construct Inhibits Pancreatic Tumor Dissemination in the Murine Peritoneal Cavity." *Cancer Research*, 55:3810-3816.

Ausuker et al., Editions Short Protocols in Molecular Biology John Wiley & Sons, New. York pp. 72-80, 1989.

Barz et al., (1985) "Characterization of cellular and extracellular plasma membrane vesicles from a non-metastasizing lymphoma (Eb)and its metastasizing variant (EESb)." *Biochimica et Biophysica Acta*, 814:7-84.

Blackburn et al., (1991) "Electrochemiluminescence Detection of Immunoassays and DNA Probe Assays for Clinical Diagnostics." *Clin. Chem.*, vol. 37, No. 9, pp. 1534-1539.

(Continued)

*Primary Examiner*—Kenneth R. Horlick
(74) *Attorney, Agent, or Firm*—McDonnell Boehnen Hulbert & Berghoff

(57) ABSTRACT

This invention relates to the detection of extracellular papillomavirus DNA in blood plasma or serum from a human or animal. In particular, the invention relates to the detection, identification, evaluation, or monitoring of neoplastic, premalignant or malignant disease associated with a papillomavirus. The invention thereby provides methods for the identification of individuals at risk for, or having, cervical dysplasia, cervical intraepithelial neoplasia, or cervical cancer.

11 Claims, 1 Drawing Sheet

OTHER PUBLICATIONS

Bobo et al., (Sep. 1990) "Diagnosis of Chylamydia trachomatis Cervical Infection by Detection of Amplified DNA with and Enzyme Immunoassay." *Journal of Clinical Microbiology*, vol. 28, No. 9, 1968-973.

Boland, Richard, (Sep. 1996) "Setting microsatellites free" *Nature Medicine*, vol. 2, No. 9, pp. 972-974.

Boom et al., (Mar. 1990) "Rapid and Simple Method for Purification of Nucleic Acids." *Journal of Clinical Microbiology*, vol. 28, No. 3, pp. 495-303.

Boom et al., (Sep. 1991) "Rapid Purification of Hepatitis B Virus DNA from Serum." *Journal of Clinical Microbiology*, vol. 29, No. 9, pp. 1804-1811.

Bos et al., (May 1987) "Prevalence of ras gene mutations in human colorectal cancers." *Nature*, vol. 327, pp. 293-297.

Carr et al., (Nov. 1985) "Circulating Membrane Vesicles In Leukemic Blood." *Cancer Research*, 45: 5944-5951.

Chaubert et al., (1994) "K-ras Mutations and p53 Alterations in Neoplastic and Nonneoplastic Lesions Associated with Longstanding Ulcerative Colitis." *Amer. Jrnl. Of Path.*, vol. 144, No. 4, pp. 767-774.

Chen et al., (1991) "A Method to Detect ras Point Mutations in Small Subpopulations of Cells." *Analytical Biochemistry*, 195: 51-56.

Chen et al., (Sep. 1996) "Microsatellite alterations in plasma DNA of small cell lung cancer patients." *Nature Medicine*, vol. 2, No. 9, pp. 1033-1035.

Chen et al., "Detecting Tumor-related Alteractions in Plasma or Serum DNA of patients Diagnosed with Breast Cancer," Clinical Cancer Research, Sep. 1999 vol. 5, 2297-2302.

Cheung et al., (Oct. 1994) "Rapid and Sensitive Method for Detection of Hepatitis C Virus RNA by Using Silica Particles." vol. 32, No. 10, pp. 2593-2597.

Chomczynski, Piotr, (1993) "A Reagent For the Single-Step Simultaneous Isolation of RNA, DNA and Proteins from Cell and Tissue Samples." *Biotechniques*, vol. 15, No. 3, pp. 532-536.

Christa et al ., (1992) "Nested polymerase chain reaction of cellular DNA in plasma: a rapid method to investigate th collagen type I A2 MspI polymorphic restriction site in alcoholic patients." *Human Genetics*, 88: 537-540.

Chua et al., 1996, Int. J. Cancer, 69: 54-59.

Cleary et al., "Cloning and Structural Analysis of cDNAs for bcl-2 and a Hybrid bcl-2/Immunoglobulin Transcript Resulting from the t(14;18) Translocation," Cell. 47:19-28, Oct. 10, 1985.

Coutlee et al., (1989) "Immunodetection of DNA with Biotinylated RNA Probes: A Study of Reactivity of a Monoclonal Antibody to DNA-RNA Hybrids." *Analytical Biochemistry*, 181: 96-105.

DiCesare et al., (1993) "A High-Sensitivity Electrochemiluminescence-Based Detection System for Automated PCR Product Quantitation." *BioTechniques*, vol. 15, No. 1, pp. 152-157.

Emanuel et al., (1993) "Amplification of Specific Gene Products from Human Serum." *GATA*, vol. 10, No. 6, pp. 144-146.

Fearon et al., (Jun. 1990) "A Genetic Model for Colorectal Tumorigenesis." *Cell*, vol. 61, pp. 759-767.

Fearon et al., (Oct. 1987) "Clonal Analysis of Human Colorectal Tumors." *Science*, vol. 238, pp. 193-196.

Fedorov et al., (1987) DNA Assay In Human Blood Plasma. Translated from *Byuleten Eksperimentsl Biologii i Meditsiny*, vol. 102, No. 9, pp. 281-281.

Fey et al., (1991) "The Polymerase Chain Reaction: A New Tool for the Detection of minimal Residual Disease In Haematological Malignancies." *Eur. J. Cancer.*, vol. 27, No. 1, pp. 89-94.

Finney et al., (Jun. 1993) "Predisposition of Neoplastic Transformation Caused by Gene Replacement of H-ras1." *Science*, vol. 260, pp. 1524-1527.

Fournie et al., (1986) "Recovery of Nanogram Quantities of DNA from Plasma and Quantitative Measurement Using Labeling by Nick Translation." *Analytical Biochemistry*, 158: 220/256.

Fournie et al., (Feb. 1995) "Plasma DNA as a marker of cancerous cell death. Investigation in patients suffering from lung cancer and in nude mice bearing human tumours." *Cancer Letters*, 91: 221-227.

Fowke et al., (1995) "Genetic analysis of human DNA recovered from minute amounts of serum of plasma." *Journal of Immunological Methods*, 180, pp. 45-51.

Gocke et al., "p53 and APC Mutations are Detectable in the Plasma and Serum of Patients with Colorectal Cancer (CRC) or Adenomas," Annals New York Academy of Sciences, p. 44-50.

Gocke et al., "Serum BCL2/IGH DNA in Follicular Lymphoma Patients: A Minimal Residual Disease Marker," Leukemia and Lymphoma 2000, 39 (1-2) pp. 165-172.

Greenblatt et al., (1994) "Mutations in the p53 Tumor Suppressor Gene: Clues to Cancer Etiology and Molecular Pathogenesis." *Cancer Research*, 54:4855-4878.

Hamiliton, Stanley., (Sep. 1992) "Molecular Genetics of Colorectal Carcinoma." *Cancer Supplement*, vol. 70, No. 5, pp. 1216-1221.

Hollstein et al., (1994) "Database of p53 gene somatic mutations in human tumors and cell lines." *Nucleic Acids Research*, vol. 22, No. 17, pp. 3551-3555.

Juckett et al., (Sep. 1982) "Actions of cis-Diamminedichloroplatinum on Cell Surface Nucleic Acids in Cancer Cells as Determined by Cell Electrophoresis Techniques." *Cancer Research*, 42: 3565-3573.

Kahn et al., (1991) "Rapid and sensitive nonradioactive detection of mutant K-ras genes via 'enriched' PCR amplification." *Oncogene*, 6: 1079-1083.

Kamm et al., (1972) "Nucleic Acid Concentrations in Normal Human Plasma." *Clinical Chemistry*, vol. 18, No. 6, pp. 519-522.

Karet et al., (1994) "Quantification of mRNA in Human Tissue Using Fluorescent Nested Reverse-Transcriptase Polymerase Chain Reaction." *Analytical Biochemistry*, 220: 384-390.

Kievits et al., (1991) "NASBA isothermal enzymatic in vitro nucleic acid amplification optimized for the diagnosis of HIV-1 infection." *Journal of Virological Methods*, 35: 273-286.

Kimura et al., 1991, J. Infect Dis. 164:289-293.

Kopreski et al., Somatic Mutation Screening: Identification of Individuals Harboring K-ras Mutations with the Use of Plasma DNA, Journal of the National Cancer Institute, vol. 92, No. 11, Jun. 7, 2000.

Kondo et al., (Mar. 1994) "Detection of Point Mutations in the K-ras Oncogene at Codon 12 in Pure Pancreatic Juice for Diagnosis of Pancreatic Carcinoma." *Cancer*, vol. 23, No. 6, pp. 1589-1594.

Landergren Trends or Genetics 9:199-204, Jun. 1993.

Landgraf et al., (1991) "Direcct Analysis of Polymerase Chain Reaction Products Using Enzyme-linked Immunosorbent Assay Techniques." *Analytical Biochemistry*, 198:86-91.

Landgraf et al., (1991) "Quantitative Analysis of Polymerase Chain Reaction (PCR) Products Using Primers Labeled with Biotin and a Fluorescent Dye." *Analytical Biochemistry*, 193: 231-235.

Lefort et al., "Point mutations of the K-Ras gene present in the DNA of colorectal tumors are found in the blood plasma DNA of the patients," Proceedings of the American Association for Cancer Research Annual. 36:557, 1995.

Leon et al., (1981) "A Comparison of DNA and DNA-Binding Protein Levels in Malignant Disease." *Europ. J. Cancer*, vol. 17, No. 5, pp. 533-538.

Leon et al., (Mar. 1977) "Free DNA in the Serum of Cancer Patients and the Effect of Therapy." *Cancer Research*, 37: 646-650.

Lowry et al., (Nov. 1991) "Regulation of p21ras Activity." *Trends of Genetics*, 7: 346-351.

Martin et al., (1992) " A Method for Using Serum of Plasma as a Source of DNA or HLA Typing." *Human Immunology*, 33: 108-113.

Mayall et al., J. Clin. Pathol. 1998, 51:611-613.

Mulcahy et al., (Sep. 1996) "Cancer and mutant DNA in blood plasma." *Science*, vol. 348, pp. 628.

Mulcany et al., "A Prospective Study of K-ras Mutations in the Plasma of Pancreatic Cancer Patients," Clinical Cancer Research, 4:271-5 (Feb. 1998).

Nawroz et al., (Sep. 1996) "Microsatellite alterations in serum DNA of head and neck cancer patients." *Nature Medicine*, vol. 2, No. 9, pp. 1035-1037.

Nelson et al., (Feb. 1996) "Detection of K-ras gene mutations in non-neoplastic lung tissue and lung cancers," *Cancer Letters* 103 (1996) 115-121.

Olsen et a., 1996, Int. J. Cancer 68:415-419.

Oudejans et al., (1991) "Differential Activation of RAS Genes By Point Mutation In Human Colon Cancer With Metastases To Either Lung of Liver." *Int. J. Cancer*, 49: 875-879.

Pellegata et al., (1992) "Detection of K-ras Mutations by Denaturing Gradient Gel Electrophoresis (DGGE): A Study of Pancreatic Cancer." *Anticancer Research*, 12:1731-1736.

Procrand et al. Mutation Research 288:113-121, Jul. 1993.

Rex et al., Gastroenterology 1997; 11:24-28.

Rhodes et al., (1995) "PCR-Detection of Tumor-Derived p53 DNA in Cerebrospinal Fluid." *Am. J. Clin. Path.*, 103:404-408.

Shapiro et al., (Jun. 1983) "Determination of Circulating DNA Levels in Patients with Benign or Malignant Gastrointestinal Disease." *Cancer*, vol. 51, No. 11, pp. 2116-2120.

Shirasawa et al., (Apr. 1993) "Altered Growth of Human Colon Cancer Cell Lines Disrupted at Activated Ki-ras." *Science*, vol. 260, pp. 85-88.

Sidransky et al., (1992) "Identification of ras Oncogene Mutations in the Stool of Patients with Curable Colorectal Tumors." *Science*, vol. 256, pp. 102-105.

Sidransky et al., "What we know and what we need to learn," Annals new York Academy of Sciences, pp. 1-4.

Sorenson et al., (Jan. 1994) "Soluble Normal and Mutated DNA Sequence from Single-Copy Genes in Human Blood." *Cancer Epidemiology, Biomarkers & Prevention*, vol. 3, pp. 67-71.

Sorenson et al., Detection of Mutated KRAS2 Sequences as Tumor Markers in Plasma/Serum of Patients with Gastrointestinal Cancer, Clinical Cancer Research, 6:2129-37 (Jun. 2000).

Stork et al., (1991) "Detection of K-ras mutations in pancreatic and hepatic neoplasms by non-isotopic mismatched polymerase chain reaction." *Oncogene*, 6:857-862.

Stroun et al., (1986) "Isolation and Characterization of DNA from the Plasma of Cancer Patients." *European Journal of Cancer*, vol. 23, No. 6, pp. 707-712.

Stroun et al., (1989) "Neoplastic Characteristics of the DNA Found in the Plasma of Cancer Patients." *Oncology*, 46: 318-322.

Tada et al., (Jun. 1993) "Detection of ras Gene Mutations in Pancreatic Juice and Peripheral Blood of Patients with Pancreatic Adenocarcinoma." *Cancer Research*, 53:2472-2474.

Taylor et al., (Date Unknown) "Shedding of Plasma Membrane Fragements. Neoplastic and Development Importance." *Membrane Fragment Shedding*, Chapter 3, pp. 33-57.

Tseng et al., 1999, J. Clin. Oncol. 17:1391-1396.

Urdea et al., (1991) "Branched DNA amplification multimers for the sensitive, direct detection of human hepatitis viruses." *Nucleic Acids Research*, Symposium Series No. 24, pp. 197-200.

Urdea et al., (1993) Direct and quantitative detection of HIV-1 RNA in human plasma with a branched DNA signal amplification assay. *Aids*, 7 (suppl. 2): S11-S14.

Vandamme et al., (1995) "Detection of HIV-1 RNA in plasma and serum samples using the NASBA amplification system compared to RNA-PCR." *Journal of Virological Methods*, 52:121-132.

Van Mansfeld et al., "PCR-based Approaches for Detection of Mutated ras Genes," PCR Methods and Applications, pp. 211-216.

Vasioukhin et al., (1994) "Point mutations of the N-ras gene in the blood plasma DNA of patients with myelodysplastic syndromes of acute myelogenous leukemia." *British Journal of Haematology*, 86: 774-779.

Vasyukhin et al., (Date Unknown) "K-Ras Point Mutations in the Blood Plasma DNA of Patients with Colorectal Tumors."

Vogelstein et al., (Sep. 1988) "Genetic Alterations During Colorectal-Tumor Development." *The New England Journal of Medicine*, vol. 319, No. 9, pp. 525-532.

Wang et al., (Dec. 1989) "Quantitation of mRNA by the polymerase chain reaction."*Proc. Natl. Acad. Sci.*, vol. 86, pp. 9717-9721.

Winawer et al., The New-Eng. Journal of Medicine vol. 328, No. 13:901-906.

Yamagata et al., (Feb. 1994) "Lower Incidence of K-ras Codon 12 Mutation in Flat Colorectral Adenomas than in Polypoid Adenomas." *Jpn. J. Cancer Res.*, 85: 147-151.

\* cited by examiner

SEQUENCE LISTING

<160> NUMBER OF SEQ ID NOS: 2

<210> SEQ ID NO 1
<211> LENGTH: 34
<212> TYPE: DNA
<213> ORGANISM: cottontail rabbit papillomavirus

<400> SEQUENCE: 1
cgggatcccg ctggaatagt taatcttctt ccgc                              34

<210> SEQ ID NO 2
<211> LENGTH: 25
<212> TYPE: DNA
<213> ORGANISM: cottontail rabbit papillomavirus

<400> SEQUENCE: 2
agctggatcc atgggacctg cagag                                        25

METHODS FOR DETECTING PAPILLOMAVIRUS DNA IN BLOOD PLASMA AND SERUM

This application is a divisional of U.S. Ser. No. 09/653,644, filed Aug. 31, 2000, now U.S. Pat. No. 6,511,805, issued Jan. 28, 2003, which is a continuation-in-part of U.S. patent application Ser. No. 09/456,222, filed Dec. 7, 1999, now U.S. Pat. No. 6,630,301, issued Oct. 27, 2003, which is a continuation-in-part of U.S. patent application Ser. No. 09/049,234, filed Mar. 27, 1998, now abandoned, which is a continuation-in-part of U.S. patent application Ser. No. 08/818,058, filed Mar. 14, 1997, now U.S. Pat. No. 6,156,504, which is a continuation-in-part of U.S. Provisional Application, Ser. No. 60/028,180, filed Oct. 15, 1996, which is a continuation-in-part of U.S. Provisional Application, Ser. No. 60/026,252, filed Sep. 17, 1996, which is a continuation-in-part of U.S. Provisional Application, Ser. No. 60/013,497, filed Mar. 15, 1996, the entire disclosure of each of the foregoing is hereby incorporated by reference.

BACKGROUND OF THE INVENTION

1. Field of the Invention

This invention relates to methods for detecting specific extracellular nucleic acid in plasma or serum fractions of human or animal blood associated with neoplastic or proliferative disease. Specifically, the invention relates to detection of nucleic acid derived from human viruses associated with human neoplasia, and to methods of detecting and monitoring extracellular viral nucleic acids found in the plasma or serum fraction of blood by using nucleic acid amplification with or without enrichment for viral DNA. In particular, the invention relates to the detection, identification, or monitoring of the existence, progression or clinical status of human neoplastic disease caused by or associated with viral infection through detection of viral nucleic acid in plasma or serum fractions. The invention permits the detection of extracellular, viral nucleic acid in the serum or plasma of humans or other animals recognized as having a neoplastic or proliferative disease or in individuals without any prior history or diagnosis of neoplastic or proliferative disease. The invention specifically provides methods for early identification of cervical carcinoma, cervical carcinoma in situ, cervical dysplasia, cervical intraepithelial neoplasia (CIN) and penile squamous cell carcinoma associated with infection by oncogenic human papillomavirus subtypes.

2. Background of the Related Art

Cervical carcinoma is a common form of malignancy afflicting women, arising from the squamous epithelium of the cervix. Much is known of the natural history of this disease. The vast majority of cases are attributable, at least in part, to an infection by a papillomavirus of the cervical epithelium. In particular, certain subtypes of human papillomavirus (HPV), including HPV subtypes 16, 18, 31, 33, and 35, are associated with cervical malignancy, where HPV infection seems to alter the epithelium to predispose an individual to the development of cancer. This alteration of the epithelium by viral infection initially leads to cervical premalignant states, specifically cervical dysplasia or cervical intraepithelial neoplasia (CIN). Cervical dysplasia/CIN is important for recognizing, diagnosing, and treating women at risk for developing cervical cancer, because surgical removal of dysplastic epithelium reduces and may even eliminate the risk of development of cervical cancer.

A prominent advance over the past several decades has been the reduction of the incidence of cervical carcinoma in the United States. In general, this advance has been attributed to the routine gynecologic examination and the introduction of the Pap smear, based upon cervical cytology. A scraping of the cervical epithelium is taken and eventually smeared on a glass slide for staining and microscopic examination. These procedures, typically carried out in a medical clinic by skilled personnel and forwarded to a laboratory for examination by technologists or specially developed machines, are useful in identifying early premalignant states. Surgical removal or destruction of the affected portion of the cervix can then be undertaken by a gynecologist, resulting in a marked reduction in the risk of development of carcinoma (although potentially associated with difficulty in child-bearing or infertility). Unfortunately, the Pap smear does not detect all instances of cervical dysplasia or premalignancy. The current acceptable rate of false negatives (i.e., women who do have dysplasia according to an expert panel of pathologists looking at tissue biopsies rather than smear samples, but are not diagnosed that way during the routine smear screening) is roughly 5–10% but recent studies suggest that the actual rate may be much higher. Furthermore, in approximately 7–8% of cases, the Pap smear demonstrates a typical squamous cells of undetermined significance (ASCUS). In an additional 20–30% of cases, the Pap smear may be insufficient for interpretation due to the presence of inflammatory cells.

Human papilloma virus (HPV) is a papillomavirus that very frequently infects a number of human tissues, including cervical tissue, and infection of cervical tissues is associated with the development of cervical carcinoma. The changes in cervical tissues attributable to viral infection are not visible to the unaided eye, but viral infection is evident at the microscopic level by changes in the epithelial cell's nucleus and cytoplasm that can be detected in a Pap smear. However, HPV infection cannot be detected in all cases of cervical dysplasia/pre-malignancy or even of cervical carcinoma. At least some of the failure to detect premalignancy using Pap smears as discusses above are the result of failure to detect HPV infection in cervical tissue samples.

HPV has many subtypes, and the subtypes may be distinguished by several methods. One commonly used method for evaluating exposure in humans to specific HPV subtypes, including those associated with cervical cancer, is by testing serum for antibodies against the viral subtype. Unfortunately, this method identifies both individuals with prior HPV exposure but without persistent infection and those with persistent infection, but does not distinguish between ongoing, persistent, and chronic HPV infections. This distinction is important, because persistent infection with HPV is associated with the greatest risk for development of cervical neoplasia. Because only a small percentage of women will develop cervical cancer within ten years of infectious exposure, active HPV infection is eliminated prior to the development of cervical premalignancy for most exposed women (Chua et al., 1996, *Int. J. Cancer* 68: 54–59). Serologic testing for HPV antibodies thus does not correlate well with the presence of cervical dysplasia, because it does not permit discrimination between previous HPV exposure and persistent HPV infection (Olsen et al., 1996, *Int. J. Cancer* 68: 415–419).

A second common method for screening women for specific HPV subtypes detects double stranded DNA viral genome (see, for example, Manos, U.S. Pat. No. 5,705,627; Bauer, U.S. Pat. No. 5,639,871; Bauer, U.S. Pat. No. 5,527,898; Manos, U.S. Pat. No. 5,283,171; Manos, U.S. Pat. No. 5,182,377; Gravitt et al., 1998, *J. Clin. Microbiol.* 36: 3020–3027). Those subtypes particularly associated with cervical cancer may be specifically amplified and detected using nucleic acid amplification methods, thereby identifying humans at high risk for the development of cervical carcinoma. Current methods for detecting HPV DNA entail evaluating cervical smear specimens directly for the viral DNA (see Silverstein, U.S. Pat. No. 5,814,448). This method is disadvantageous because the examiner may miss an infected region of the cervix, or the infected lesion may not be superficial and readily accessible, so that the test provides a false-negative result. Furthermore, as this method of testing for HPV DNA requires a gynecologic exam, DNA testing of cervical smears remains an imperfect method of screening the general female population because such exams are avoided by many women despite medical recommendations to the contrary.

In addition, HPV infection is a sexually transmitted disease, and males may carry the virus as asymptomatic carriers. Typically, cervical infection takes place at the time of sexual intercourse, and most of the risk factors (unprotected intercourse, multiple sexual partners, immunodeficiency, etc.) that apply to other sexually transmitted diseases also apply to HPV infection. Men may be infected by one or more HPV subtypes and can transmit one or more of these to their sexual partners. Although in most instances men serve only as carriers of the viral infection, in relatively rare cases they may develop squamous cell carcinoma of the penis in a manner analogous to cervical dysplasia and carcinoma in women. Both sexes may also develop ano-genital warts, called condyloma accuminata, if infected by certain species of HPV, and these lesions may also be premalignant. Direct tissue swabs of the male urethra are not an effective general screening approach for detecting such carriers in the male population.

An attractive alternative approach to detecting HPV DNA in both women and men is testing peripheral blood for HPV DNA. However, it is not known in the art that papillomavirus DNA can be detected in the blood of individuals without cancer. Further, it is not known to the art whether papilloma virus can be detected in plasma and serum as an indication of persistent infection or risk for dysplasia or carcinoma.

Although many viruses have been shown to circulate in plasma and serum, the presence of systemically circulating extracellular HPV DNA has not been described in either the acute or chronic HPV infection. HPV infections tend to be localized as intracellular epithelial infections, and do not typically present with systemic clinical manifestations. Although metastatic circulating cervical cancer cells and leukocytes have been shown to have intracellularly incorporated HPV in cases of advanced cancer (Tseng et al., 1999, *J. Clin. Oncol.* 17: 1391–1396), detection of extracellular or free HPV DNA in blood is unknown in the art. To the contrary, the prior art suggests that some viruses are not readily detectable in the blood of infected individuals. An example is herpes simplex virus, which like HPV is a sexually-transmitted virus spread by mucosal contact. It was known in the art that, although herpes simplex virus could be found in blood serum of neonates with neonatal herpes simplex viremia, such could not be found in serum from older children having herpes simplex encephalitis, despite the presence of the virus in the cerebrospinal fluid of these older children (Kimura et al., 1991, *J. Infect. Dis.* 164: 289–293). In addition, HPV does not present with systemic viremia, and even for viruses in which viremia has been reported, the likelihood of detecting systemic viremia is greatest near the time of initial infection. This makes screening of women for the HPV virus doubly impractical, since any such screening would most likely be performed well beyond the period of initial exposure to the virus in the majority of cases.

One of the present inventors has shown that tumor-associated extracellular nucleic acids circulate in the plasma and serum of humans and animals (U.S. Ser. No. 08/818,058, the entire disclosure of which has been incorporated by reference). In particular, this application disclosed that tumor-associated DNA could be detected in the plasma and serum of humans and animals without cancer, enabling premalignancy to be detected, diagnosed, and monitored, and further, that individuals without cancer could be stratified or selected for further evaluation on the basis of the presence of mutant oncogene-derived DNA in blood plasma or serum.

Thus, there is a need in the art to determine whether HPV-specific nucleic acid can be detected in blood plasma or serum, and whether detection of HPV nucleic acid can be associated with the existence of cervical dysplasia or premalignancy. Improved screening methods having advantages over gynecological examinations and Pap smears would be enabled upon such a demonstration.

SUMMARY OF THE INVENTION

The present invention provides methods for detecting extracellular papillomavirus nucleic acid in blood or blood plasma or serum in a human or animal. The methods of the invention comprise the steps of extracting the nucleic acid from blood, plasma, or serum, specifically amplifying a portion of the extracted nucleic acid wherein the portion comprises a papillomavirus nucleic acid or a fragment thereof, and detecting the amplified product of the papillomavirus nucleic acid or fragment.

In a first aspect, the present invention provides methods for detecting papillomavirus DNA in blood or blood fractions, including plasma and serum, in a human or animal for detection, diagnosis, monitoring, treatment, or evaluation of neoplastic disease, including early cancer, non-invasive cancer, carcinoma in-situ, premalignancy, invasive cancer, and advanced cancer. In this aspect, the method comprise the steps of extracting DNA from blood or blood plasma or serum, amplifying a fraction of the DNA wherein said fraction comprises papillomavirus DNA, and detecting the amplified product of papillomavirus DNA.

The invention further provides methods for detecting extracellular papillomavirus DNA in bodily fluids other than those of the genital-urinary tract, including but not limited to whole blood, plasma, serum, effusions, ascitic fluid, saliva, cerebrospinal fluid, gastrointestinal secretions, and bronchial secretions including sputum, from a human for detection, diagnosis, monitoring, treatment, or evaluation of neoplastic disease, including early cancer, non-invasive cancer, carcinoma in-situ, premalignancy, invasive cancer, and advanced cancer. In these embodiments, the methods comprise the steps of extracting DNA from said bodily fluid, amplifying a fraction of the DNA wherein said fraction comprises papillomavirus DNA, and detecting the amplified product of papillomavirus DNA.

The invention further provides methods for detecting papillomavirus RNA in blood or blood fractions, including plasma and serum, in a human or animal for detection, diagnosis, monitoring, treatment, or evaluation of neoplastic disease, including early cancer, non-invasive cancer, carcinoma in-situ, premalignancy, invasive cancer, and advanced cancer. In these embodiments, the methods comprise the steps of extracting RNA from blood or blood plasma or serum, enzymatically converting the RNA into cDNA, amplifying a fraction of the cDNA wherein said fraction comprises papillomavirus cDNA, and detecting the amplified product thereof.

The invention further provides methods for detecting extracellular papillomavirus RNA in bodily fluids other than those of the genital-urinary tract, including but not limited to whole blood, plasma, serum, effusions, ascitic fluid, saliva, cerebrospinal fluid, gastrointestinal secretions, and bronchial secretions including sputum, from a human as an aid in the detection, diagnosis, monitoring, treatment, or evaluation of neoplastic disease, including early cancer, non-invasive cancer, carcinoma in-situ, premalignancy, invasive cancer, and advanced cancer. In these embodiments, the methods comprise the steps of extracting RNA from said bodily fluid, enzymatically converting the RNA into cDNA, amplifying a fraction of the cDNA wherein said fraction comprises papillomavirus cDNA, and detecting the amplified product of papillomavirus RNA.

The invention provides a diagnostic kit enabling detection of papilloma virus nucleic acid in blood or other bodily fluids, wherein the kit comprises primers specific for amplifying a fragment of human papillomavirus DNA, and optionally further comprises reagents, including salts, buffers, deoxynucleotide triphosphates or solutions thereof, and preparations of a polymerase, most preferably a thermostable polymerase, for amplifying said human papillomavirus nucleic acid fragments. In alternative embodiments, the kits further comprise salts, buffers, deoxynucleotide triphosphates or solutions thereof, and preparations of an enzyme, most preferably reverse transcriptase, for converting human papillomavirus RNA into cDNA.

The invention further provides methods for detecting extracellular papillomavirus nucleic acid, including HPV DNA and RNA, in blood, plasma, serum, and other bodily fluids, without amplification of the nucleic acid, for detection, diagnosis, monitoring, or evaluation of malignant or premalignant disease, including malignancies and premalignancies of the cervix. In these embodiments, the methods comprise the steps of extracting nucleic acid from blood or a blood fraction, specifically plasma or serum, to prepare extracted nucleic acid; specifically hybridizing a probe to a portion of the extracted nucleic acid, wherein the portion of the extracted nucleic acid is a papillomavirus nucleic acid; and detecting the hybridized papillomavirus nucleic acid. In preferred embodiments, nucleic acid extraction may be performed concurrently with hybridization of nucleic acid. In preferred embodiments, said hybridization is performed at a stringency sufficient for the probe to specifically hybridize to papillomavirus DNA and not non-specifically cross-hybridize to non-papillomavirus DNA.

In preferred embodiments of the inventive methods, papillomavirus DNA is extracted from blood plasma or serum using an extraction method selected from a group consisting of gelatin extraction method; silica, glass bead, or diatom extraction method; guanidinium thiocyanate acid-phenol based extraction methods; guanidinium thiocyanate acid based extraction methods; centrifugation through a cesium chloride or similar gradient; phenol-chloroform based extraction methods; or other commercially available nucleic acid extraction methods.

In preferred embodiments of the inventive methods, papillomavirus DNA is amplified using an amplification method selected from a group consisting of polymerase chain reaction; ligase chain reaction; DNA signal amplification; Q-beta replication; transcription-based amplification; isothermal nucleic acid sequence based amplification; self-sustained sequence replication assays; boomerang DNA amplification; strand displacement activation; cycling probe technology; and any combination or variation thereof.

In preferred embodiments of the inventive methods, detection of the amplified papilloma virus DNA product is performed using a detection method selected from a group consisting of gel electrophoresis; ELISA detection including modifications, including biotinylated or otherwise modified primers; hybridization using a specific, fluorescent-, radioisotope-, or chromogenically-labeled probe; Southern blot analysis; electrochemiluminescence; reverse dot blot detection; and high-performance liquid chromatography.

In another preferred embodiment, the invention provides a method for evaluating a human for cervical malignancy or premalignancy, wherein the method comprises two or more tests performed either in a concurrent or sequential fashion, wherein one test evaluates plasma or serum for the presence of HPV DNA, and a second test is either a pap smear, a bimanual pelvic examination, a tissue biopsy, or a colposcopy.

The methods of the invention can identify humans or animals having persistent papillomavirus infection, thereby identifying humans at risk for developing or who have in fact developed a neoplastic, premalignant, or malignant disease associated with papillomavirus. In certain embodiments, these methods comprise the steps of extracting nucleic acid, said nucleic acid being DNA or RNA, from a bodily fluid, including but not limited to blood plasma or serum, amplifying a fraction of the extracted nucleic acid wherein said fraction comprises papillomavirus nucleic acid, detecting the amplified papillomavirus nucleic acid product; and performing said steps in a repetitive or serial manner, wherein detection of the amplified papillomavirus nucleic acid product serially or repetitively identifies a human or animal having a persistent papillomavirus infection, said human or animal thereby being at high risk for developing or having a disease associated with papillomavirus.

The methods of the invention are useful if providing a prognosis of malignant disease in a human, and for determining a predisposition to cancer in a human.

The methods of the invention comprise diagnostic methods for identifying humans at risk for developing or who have malignancy or premalignancy of the epithelium, these malignancies including but not limited to cervical, penile and squamous cancers, and these premalignancies and carcinoma in-situ including but not limited to cervical dysplasia and cervical intraepithelial neoplasia (CIN).

The methods of the invention further comprise methods to identify or select a human having an HPV-containing malignancy or premalignancy. The invention thereby provides methods to identity, stratify, or select a human who might benefit from an HPV-directed therapy, or from a further diagnostic test or therapeutic procedure, including but not limited to a bimanual pelvic exam, Pap smear, colposcopy, biopsy, endocervical currettage, conization of the cervix, and anti-viral therapies.

It is therefore the object of this invention to detect or infer the presence of papilloma virus-positive cancerous or pre-cancerous cells within a human having a recognized cancer or pre-cancer, and in those not previously diagnosed, by examining the plasma or serum fraction of blood, or examining other bodily fluid, for papilloma virus nucleic acids in either a qualitative or quantitative fashion.

One advantageous application of this invention is for identifying individuals having epithelial malignancies and premalignancies. Another advantageous application of this invention is for selecting individuals for HPV-or disease-directed therapies, including biotherapies, chemotherapies, anti-viral therapies, radiation therapies, and surgical therapies. Yet another advantageous application of the methods of this invention is to provide a marker for determining whether an adequate therapeutic effect has been achieved by a therapy, or whether additional or more advanced therapy is required, and to assess prognosis in these patients. A further advantageous application of this invention is to permit identification or analysis, either quantitatively or qualitatively, of papillomavirus nucleic acid in plasma or serum of humans during or following surgical procedures to remove premalignant or malignant lesions, and thus allow stratification of such patients as to their risk of residual cancer following the surgery, and their need for further therapy. It is also an advantageous application of this invention to allow identification or analysis of papilloma virus nucleic acid, either qualitatively or quantitatively, in the blood or other bodily fluid of a human who has completed therapy as an early indicator or relapsed cancer, impending relapse, or treatment failure. Another advantageous application of this invention is to allow identification of persistent papilloma virus infection through serial analysis of blood or body fluid samples as a method of stratifying risk of development of premalignant or malignant disease or prognosis.

Specific preferred embodiments of the present invention will become evident from the following more detailed description of certain preferred embodiments and the claims.

DETAILED DESCRIPTION OF THE PREFERRED EMBODIMENTS

Figure 1:
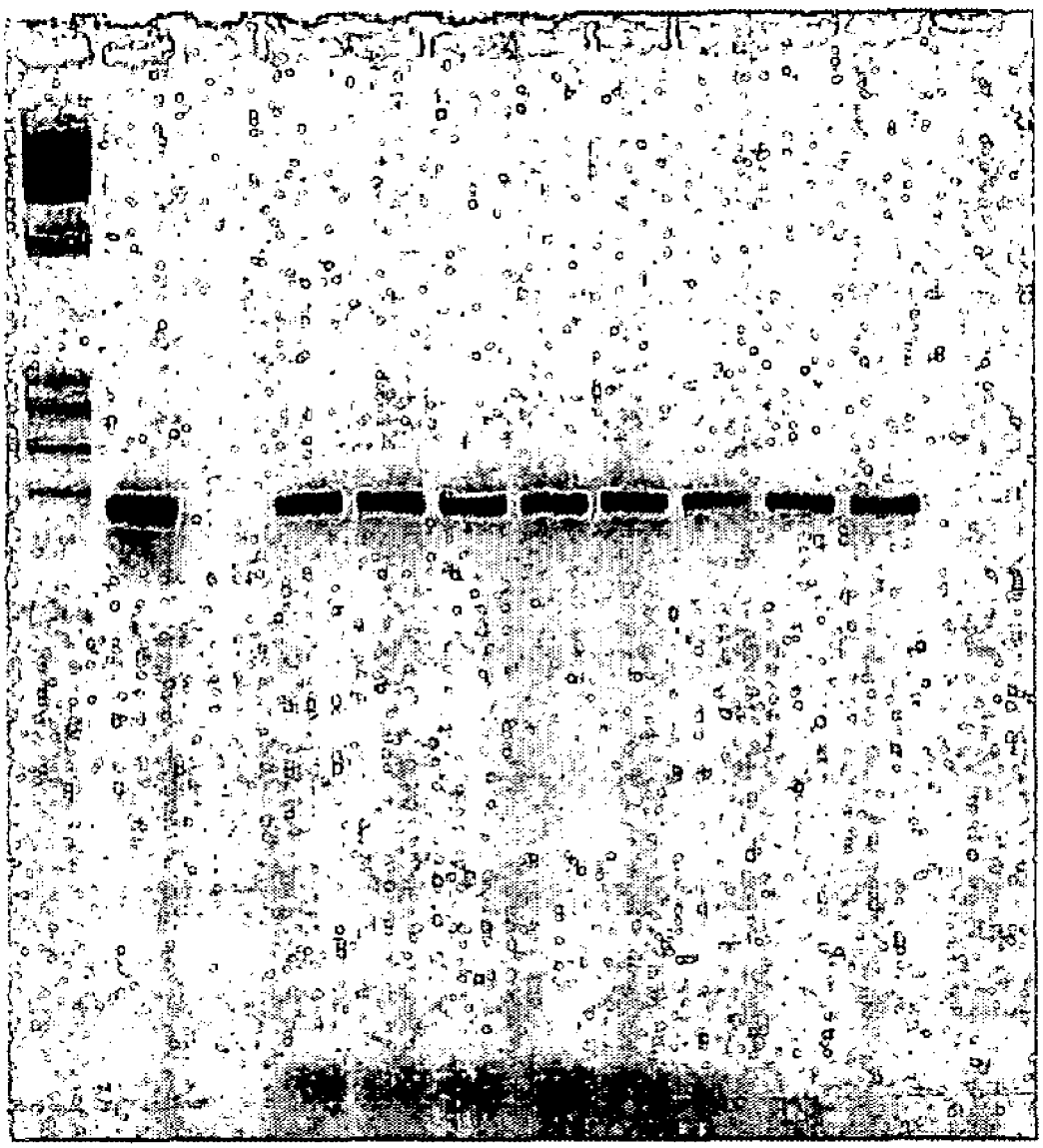
FIG. 1 is a photograph of an electrophoretic gel stained to show an amplified papillomavirus DNA fragment from rabbit blood serum obtained serially following infection. Size markers are in the left lane, the positive control in the second lane, the time zero point in the third lane, and subsequent monthly time points in the lanes following. The negative control is in the right lane.

The present invention demonstrates that extracellular viral DNA of known association to neoplasia, in particular HPV DNA, enables the detection and monitoring of premalignancy in humans without cancer or without known cancer. The present invention thereby enables the stratification or selection of humans for further evaluation on the basis of plasma or serum papillomavirus DNA status.

The present invention provides methods for detecting extracellular papillomavirus nucleic acids in the bodily fluids of human and animals. This test is particularly advantageous in detecting human papillomavirus (HPV) in plasma and serum, and can be used to detect individuals with pre-malignant or malignant disease, such as of the cervix, penis, head and neck and other sites, attributable in part to papillomavirus-associated disease. Both in isolation and in concert with other nucleic acid assays the methods of the invention are useful in diagnosing, monitoring, prognosticating and defining treatment for such diseases and the viral infection that underlies them.

The invention provides methods for detection of extracellular papillomavirus nucleic acid in blood plasma or serum from a human or animal, wherein the method consists of the steps of first purifying nucleic acid from plasma or serum to prepare extracted nucleic acid; second, specifically amplifying a portion of the extracted nucleic acid to produce an amplified fragment of papillomavirus nucleic acid; and third, detecting the amplified fragment of papillomavirus nucleic acid. In a preferred method, the nucleic acid is deoxyribonucleic acid (DNA), although the method further permits detection of viral RNA. The invention further provides methods for identifying humans or animals at high risk for papillomavirus-associated neoplasia, including humans without cancer, or without known cancer, and particularly at high risk for cervical neoplasia, wherein persistent papillomavirus infection is identified by serially testing plasma or serum for papillomavirus nucleic acid. In a particularly preferred method, the papillomavirus nucleic acid is HPV DNA. The methods of the invention may further be applied to many bodily fluids, including but not limited to blood, plasma, serum, urine, effusions, ascitic fluid, saliva, cerebrospinal fluid, gastrointestinal secretions, and bronchial secretions including sputum.

In a preferred method, nucleic acid is extracted from a bodily fluid such as plasma or serum prior to amplification. Methods of extraction are detailed in U.S. patent application Ser. No. 08/818,058, the entire disclosure of which is hereby incorporated by reference. Furthermore, any commercially-available extraction method for the efficient extraction of DNA, particularly viral DNA, from bodily fluids may be used. In a preferred embodiment of the inventive methods, papillomavirus DNA is extracted from serum using the gelatin extraction method described in U.S. Ser. No. 08/818, 058. In a preferred embodiment, blood is collected by venipuncture, and serum separated by centrifugation, for example at 1100×g for 10 minutes at 4° C. Sera or plasma may be maintained frozen, for example at −70° C. until use. DNA is extracted from the thawed serum as described, for example using a gelatin extraction method. The gelatin method of extraction is indicated by way of example, and does not serve as a limitation on the methods useful in extraction of nucleic acids, the choice of a plurality of such methods known in the art being within the skill of one having ordinary skill in the art without the exercise of undue experimentation.

Following extraction of DNA from plasma or serum or other bodily fluid, a fraction of which contains a papillomavirus DNA, and in a preferred embodiment being HPV DNA, the papillomavirus DNA is then amplified, said amplification being performed in either a qualitative or quantitative manner. Useful amplification assays are well known in the art and are detailed in U.S. Ser. No. 08/818,058, as herein incorporated by reference, and include but are not limited to polymerase chain reaction, ligase chain reaction, DNA signal amplifications such as branched DNA signal amplification, Q-beta replication, transcription-based amplification, boomerang DNA amplification, strand displacement activation, cycling probe technology, isothermal nucleic acid sequence based amplification, and other self-sustained sequence replication assays. Amplification may be performed using primers or probes specific to the papillomavirus subtypes of interest. For humans, detection of HPV can be achieved using either broad specificity amplimers that detect a large number of HPV types (either because they have degenerate positions or because they are to conserved regions of the genome, such as primer sets MY09–MY11, GP5+GP6+, and PGMY09–PGMY11 (as disclosed in Gravitt et al., 2000, *J. Clin. Microbiol.* 38: 357–361), or primer sets specific to one or a few types of HPV (such as primers specific for types 6b, 11, 16, 18, and 33). For example, but not limitation, primers or probes may be used which are specific to HPV DNA subtypes 16, 18, 31, 33, and 35, either individually, in separate reactions, or multiplexed, or within amplification chips. Primers and probes and amplifications that are known to the art may also be employed. For example, primers and probes as described by Manos et al., in U.S. Pat. No. 5,705,627; Bauer, U.S. Pat. No. 5,639,871; Bauer, U.S. Pat. No. 5,527,898; Manos, U.S. Pat. No. 5,283,171; and Manos, U.S. Pat. No. 5,12,377 can be used, where in a preferred embodiment primers are used in a polymerase chain reaction amplification. The choice of primer pairs indicated here is not intended to be all-inclusive, and many other existing or designed primer pairs would work equally well. In addition, other amplification methods such as ligase chain reaction and Q-beta replication amplification are useful for particular applications such as mRNA amplification. Alternatively, direct detection methods currently employed for identification of viral DNA and RNA in tissue samples (such as the Hybrid Capture Assay-II Digene, Silver Spring Md.) can be used on blood serum or plasma nucleic acids. Direct methods of detection not requiring amplification, wherein a probe is hybridized to papillomavirus DNA, can be employed following extraction of DNA from the bodily fluid, or simultaneously during the extraction step where extraction of DNA and hybridization of DNA occur together in a single step.

In preferred embodiments, detection of amplified products can be performed using detection methods including but not limited to those selected from a group consisting of gel electrophoresis, ELISA detection including modifications, including biotinylated or otherwise modified primers, hybridization using a specific fluorescent-, radioisotope-, or chromogenically-labeled probe, Southern blot analysis, electrochemiluminescence, reverse dot blot detection, and high-performance liquid chromatography.

In other embodiments of the invention, viral DNA is detected without first amplifying the DNA. In these embodiments are provided methods for detecting extracellular papillomavirus DNA in blood plasma or serum by purifying DNA from blood or the blood fraction, said fraction being plasma or serum, specifically hybridizing a probe to a portion of the extracted DNA, wherein the portion of extracted DNA is a papillomavirus DNA, and detecting the hybridized papillomavirus DNA.

Aspects of the invention, as relate to extraction of a papillomavirus DNA from plasma, serum, or other non-cervical bodily fluid, amplification of the DNA with specific primers or probes, and detection of the amplified product, may thereby be incorporated in whole or in part into a diagnostic kit wherein the kit aids in the detection, diagnosis, evaluation, monitoring, and/or treatment of a neoplastic disease. This kit has particular advantage for the screening of humans without cancer, and the screening of humans without known cancer. Kits provided by the invention advantageously contain reagents for performing the steps of the methods of the invention, including but not limited to reagents, including salts, buffers, deoxynucleotide triphosphates or solutions thereof, and preparations of a polymerase, most preferably a thermostable polymerase, for amplifying said human papillomavirus nucleic acid fragments. In alternative embodiments, the kits further comprise salts, buffers, deoxynucleotide triphosphates or solutions thereof, and preparations of an enzyme, most preferably reverse transcriptase, for converting human papillomavirus RNA into cDNA.

The invention provides methods for detecting papillomavirus DNA, including human papillomavirus DNA, in the blood plasma or serum, for detection, diagnosis, monitoring, treatment, or evaluation of neoplastic disease associated with papillomavirus, including HPV. Said neoplastic diseases include premalignancy, dysplasia, early cancer, non-invasive cancer, carcinoma-in-situ, invasive cancer, and advanced cancer, including cervical cancer, cervical dysplasia, and cervical intraepithelial neoplasia, and including papilloma.

In a particularly preferred embodiment, the methods of the invention may be performed in a serial manner as to assess the presence of a persistent HPV infection. In preferred embodiments, the methods of the invention identify a human or animal having a persistent papillomavirus infection, thereby permitting the assignment of a high risk of the human or animal developing a neoplastic, malignant, or premalignant disease associated with the papillomavirus. The methods of the invention thereby provide methods of determining a prognosis in a human or animal, and further, determining a predisposition to cancer in the human or animal.

The inventive methods of amplification and detection of papillomavirus DNA in plasma and serum, and other bodily fluids, are therefore useful for assigning and monitoring the course of treatment and effectiveness of both non-specific and specific therapies, procedures, and diagnostic tests pertaining to HPV infection and/or cervical malignancy and premalignancy. Said therapies include but are not limited to anti-viral therapy, biotherapy, chemotherapy, and radiation therapy. Said procedures include but are not limited to bimanual pelvic examination, surgery, biopsy, laser treatment, cryotherapy, conization of the cervix, and endocervical currettage. Said diagnostic tests include but are not limited to Pap smear and similar cytologic assessment, and colposcopy. The invention further enables stratification and selection of humans likely to benefit from specific therapy and procedures, and provides a method of monitoring response, relapse, and prognosis. Of particular value, the invention allows said stratification even when the neoplasm is premalignant, early, or occult, such as following resection or when minimal residual disease is present.

The methods of the invention and preferred uses for the methods of the invention are more fully illustrated in the following Examples. These. Examples illustrate certain aspects of the above-described method and advantageous results. These Examples are shown by way of illustration and not by way of limitation.

EXAMPLE 1

Three cottontail rabbits were infected at time zero with the cottontail rabbit papilloma virus (CRPV), a form of the virus specific to the squamous epithelium of the cottontail rabbit. The cottontail rabbit is used extensively as a model for the human version of papilloma virus infection and progression to dysplasia and carcinoma. Blood was drawn and serum separated prior to infection and approximately every month thereafter. The serum was stored frozen at −80°C. Each of the animals developed pre-malignant lesions (papillomas) approximately 5 weeks after the initial inoculation, and cancer approximately 4–13 months after time zero.

DNA was extracted from the serum by a method described in U.S. patent application Ser. No. 08/818,058. One tenth of the resulting extract was utilized in a polymerase chain reaction, also as described except that primers to the E8 region of the CRPV genome were used at 25 picomoles each per reaction. The oligonucleotide primer sequences were as follows:

```
                                        (SEQ ID No.:1)
Primer 1: 5'-CGGGATCCCGCTGGAATAGTTAATCTTCTTCCGC-3'

(SEQ ID No.:2)
Primer 2: 5'-AGCTGGATCCATGGGACCTGCAGAG-3'
```

The thermocycling parameters were: denaturation at 94° C. for one minute, annealing at 55° C. for one minute and extension at 72° C. for one minute, repeated 35 times. As a positive control, a portion of the E8 gene cloned into a plasmid was used in parallel with the test samples. Water blanks served as negative controls. Half of the resulting PCR products were electrophoresed through a 4% agarose non-denaturing gel and stained with ethidium bromide.

The results of such an experiment from one of the infected rabbits are shown in FIG. 1. Each of the rabbits was negative by PCR for the CRPV in the pre-infection specimen. Every subsequent sample (N=8, 13 and 13) gave an ethidium bromide-stained band of approximately 150 base pairs, as expected for a fragment amplified using these primers and having the E8 genome as template. These results indicated that the papillomavirus DNA could be detected in rabbit serum using the methods of the invention. PCR products from two of the rabbits were subsequently sequenced by the cycle-sequencing method and confirmed as exact matches to the E8 portion of the CRPV genome.

EXAMPLE 2

A young, sexually active woman visits her gynecologist for a routine examination. A Pap smear is obtained as standard practice, and blood for the HPV nucleic acid assay is also obtained. The Pap smear is reviewed by a cytotechnologist, who finds no abnormalities. The blood test is performed by isolating nucleic acids, both DNA and RNA, from the plasma or serum component. A broad spectrum assay for several dozen HPV types is performed by the PCR method, with detection by the hybrid capture method commonly used for testing of tissue samples for HPV. A positive result is obtained, and a portion of the PCR product is genotyped by digestion with a number of restriction endonucleases. The patient is found to have two types of virus, high risk type 18 and low risk type 4. The sample is used to quantify the mRNA for these two types and a value of 500 genomes/microliter of blood is obtained for the type 18.

In retrospect, the "normal" Pap smear may be attributable to lab error, sampling error, or the true absence of dysplastic cells on the smear. The patient is recalled and undergoes colposcopy followed by biopsy of suspicious areas. Cervical dysplasia is confirmed on the biopsy. The patient then undergoes treatment with a virus type 18 specific vaccine, resulting in stimulation of the immune system and eradication of any further type 18 viral infection.

It should be understood that the foregoing disclosure emphasizes certain specific embodiments of the invention and that all modifications or alternatives equivalent thereto are within the spirit and scope of the invention as set forth in the appended claims.

d) detecting human papillomavirus DNA in blood from a woman not having cancer but having cervical dysplasia thereby.

2. A method for detecting human papillomavirus DNA in blood from a woman not having cancer but having cervical dysplasia, the method comprising the steps of:
 a) extracting DNA from blood from a woman not having cancer but having cervical dysplasia
 b) specifically hybridizing a primer or probe to a portion of the extracted DNA comprising human papillomavirus DNA;
 c) detecting the hybridized human papillomavirus DNA; and
 d) detecting human papillomavirus DNA in blood from a woman not having cancer but having cervical dysplasia thereby.

3. A method according to claim 2, wherein the extraction of nucleic acid in subpart (a) occurs during hybridization in subpart (b) as a single step.

4. A method according to claim 1, whereby a therapy is selected or monitored.

5. A method according to claim 2, whereby a therapy is selected or monitored.

6. A method for detecting human papillomavirus RNA in blood from a woman not having cancer but having cervical dysplasia, the method comprising the steps of:
 a) extracting RNA from blood from a woman not having cancer but having cervical dysplasia;
 b) reverse transcribing the extracted RNA to cDNA;

---

---

We claim:

1. A method for detecting human papillomavirus DNA in blood from a woman not having cancer but having cervical dysplasia, the method comprising the steps of:
 a) extracting DNA from blood from a woman not having cancer but having cervical dysplasia;
 b) amplifying or signal amplifying a portion of the extracted DNA comprising human papillomavirus DNA to produce an amplified product or amplified signal of human papillomavirus DNA;
 c) detecting the amplified product or amplified signal of human papillomavirus DNA; and c) amplifying or signal amplifying a portion of the cDNA to produce an amplified cDNA product or signal of human papillomavirus RNA;
 d) detecting the amplified cDNA product or signal; and
 e) detecting human papillomavirus RNA in blood from a woman not having cancer but having cervical dysplasia thereby.

7. A method for detecting human papillomavirus RNA in blood from a woman not having cancer but having cervical dysplasia, the method comprising the steps of:
 a) extracting RNA from blood from a woman not having cancer but having cervical dysplasia;
 b) reverse transcribing the extracted RNA to cDNA;

c) specifically hybridizing a primer or probe to a portion of the cDNA, wherein the portion of cDNA is human papillomavirus cDNA;

d) detecting the hybridized cDNA; and e) detecting human papillomavirus RNA in blood from a woman not having cancer but having cervical dysplasia thereby.

8. A method according to claim 6, whereby a therapy is selected or monitored.

9. A method according to claim 7, whereby a therapy is selected or monitored.

10. A method of identifying a human or animal having a risk or predisposition for developing a papillomavirus-associated cancer or premalignancy, comprising the step of detecting extracellular papillomavirus nucleic acid in plasma or serum from the human or animal.

11. The method of claim 10, wherein the cancer is an epithelial cancer.

* * * * *